United States Patent [19]

Lawrence

[11] Patent Number: 5,796,097
[45] Date of Patent: Aug. 18, 1998

[54] CHEMICAL SENSOR AND METHOD

[75] Inventor: William R. Lawrence, Downieville, Calif.

[73] Assignee: California Lightwave Laboratories, Inc., Downieville, Calif.

[21] Appl. No.: 811,692

[22] Filed: Mar. 5, 1997

[51] Int. Cl.$^6$ .............................. H01J 5/16; G01D 5/34
[52] U.S. Cl. ................................ 250/229; 356/437
[58] Field of Search ................. 250/229, 227.21, 250/222.1; 356/436, 437, 434; 422/58

[56] References Cited

U.S. PATENT DOCUMENTS

| | | | |
|---|---|---|---|
| 4,270,049 | 5/1981 | Tanaka et al. | 250/227 |
| 4,596,443 | 6/1986 | Diemeer et al. | 350/96.23 |
| 4,795,226 | 1/1989 | Bennion et al. | 350/96.15 |
| 4,842,783 | 6/1989 | Blaylock | 264/1.4 |
| 5,015,843 | 5/1991 | Seitz et al. | 250/227.21 |
| 5,120,505 | 6/1992 | Lowell, Jr. et al. | 422/58 |
| 5,379,889 | 1/1995 | Lawrence | 250/227.16 |

*Primary Examiner*—Edward P. Westin
*Assistant Examiner*—Kevin Pyo
*Attorney, Agent, or Firm*—Flehr Hohbach Test Albritton & Herbert LLP

[57] ABSTRACT

A chemical sensor (11) including a light source (12) for producing a light flux bundle (16), an optical detector (14) for receiving a transmitted light flux bundle (24), and an absorber/expander sensor element (18) supported by a holder or support (20). Absorber/expander sensor element (18) is positioned in the space between light source (12) and optical detector (14). The absorber/expander material of sensor element (18) changes its size by either expanding or contracting in the presence of a particular chemical component. An edge (22) of sensor element (18) acts like a shutter and moves in and out of the path of travel of light flux (16), as the sensor element changes in size, which affects the intensity of light reaching and detected by optical detector (14). A method of detecting changes in the amount of a chemical analyte comprising the steps of transmitting a light flux (16) from a light source (12) past an absorber/expander (18) having a movable edge (22), exposing the absorber/expander (18) to the chemical analyte, and sensing the change in transmitted light flux (24) reaching the optical detector (14).

26 Claims, 4 Drawing Sheets

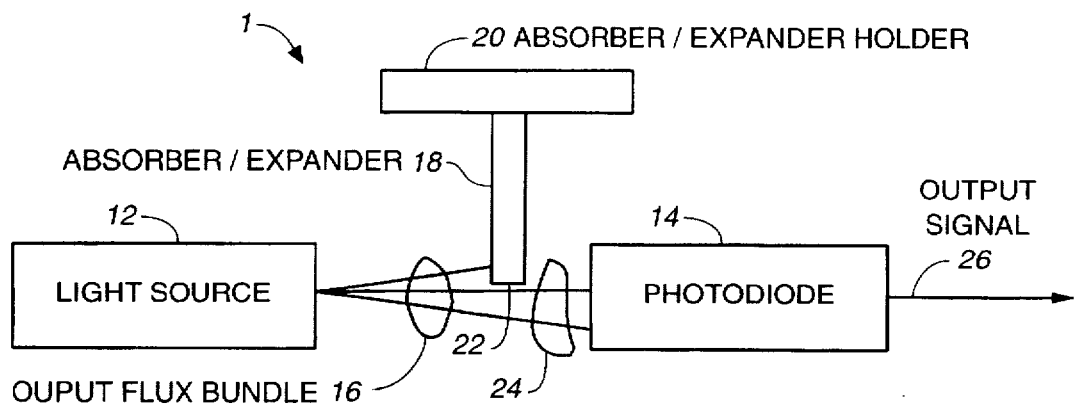
FIG._1
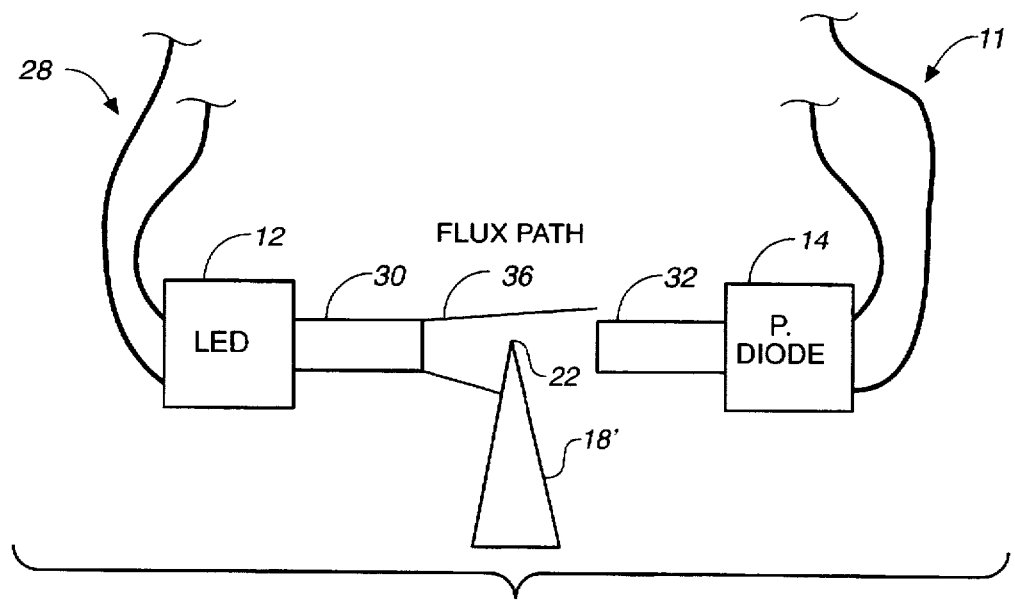
FIG._2

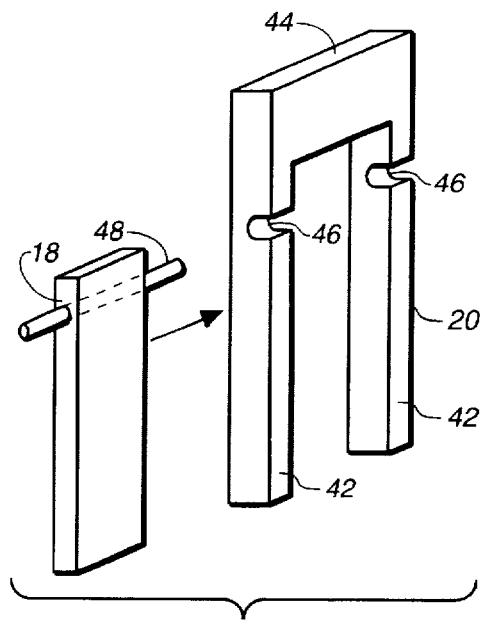
FIG._3
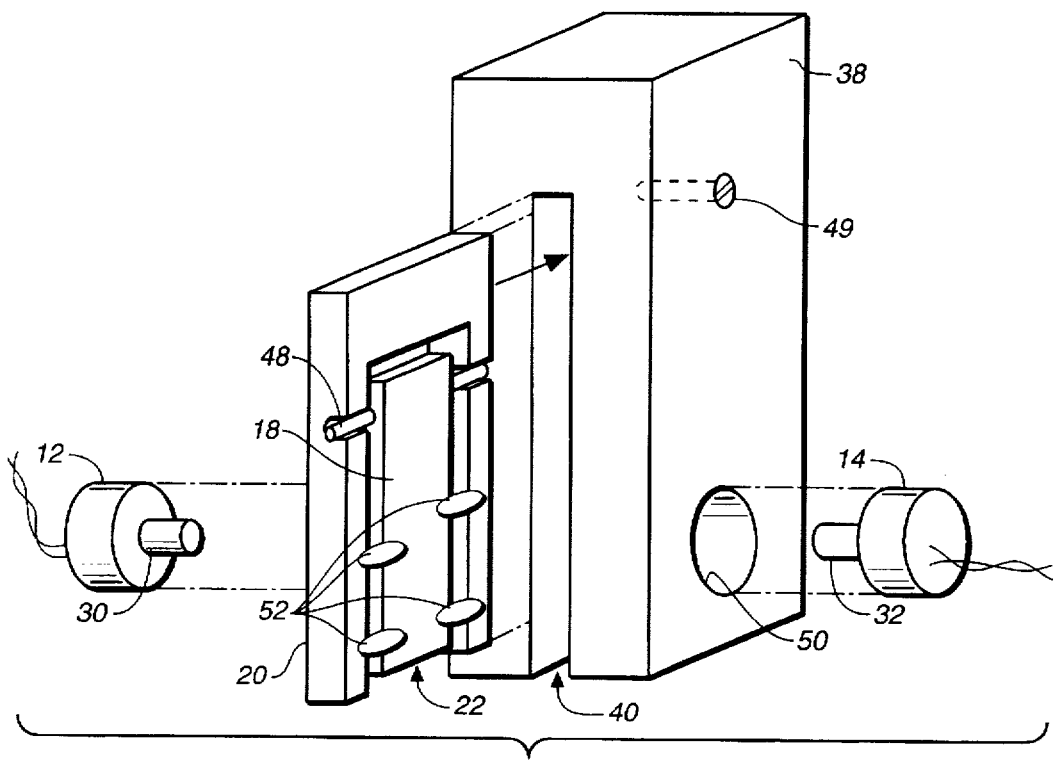
FIG._4

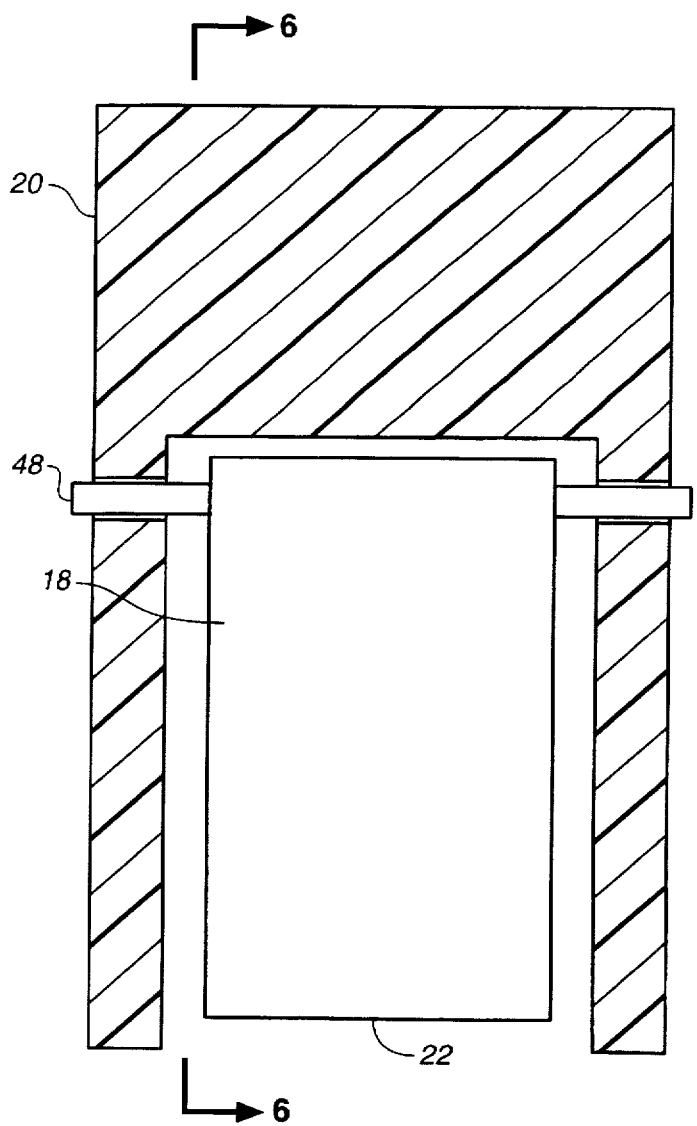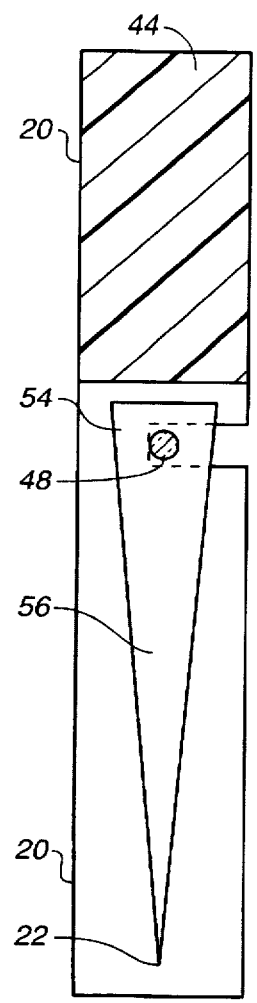
FIG._5
FIG._6

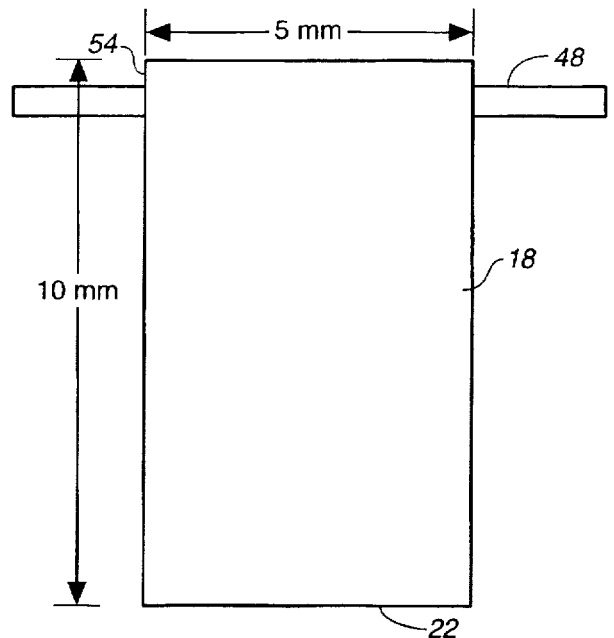
FIG._7
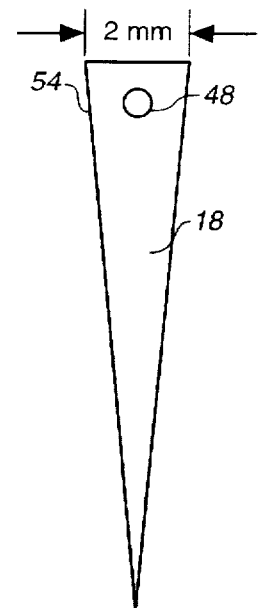
FIG._8
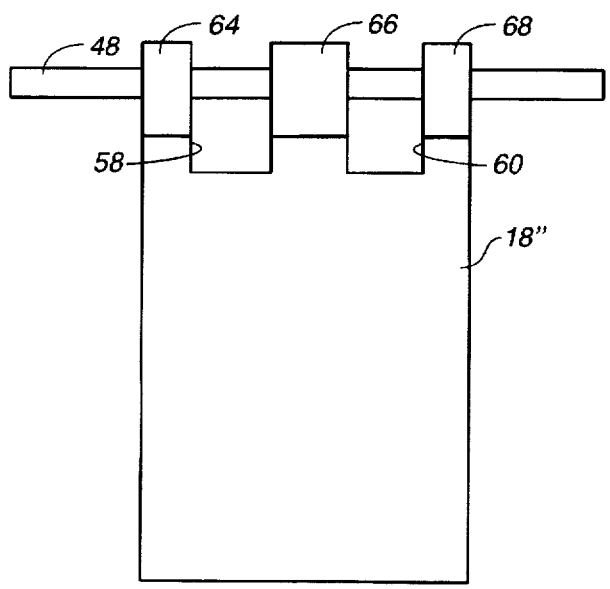
FIG._9
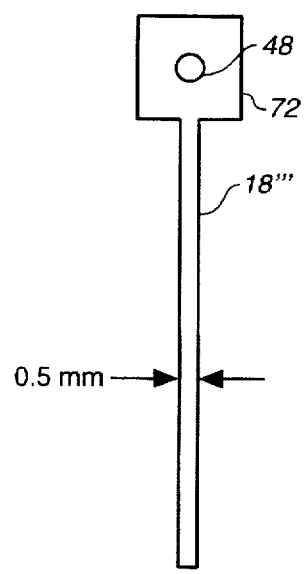
FIG._10

CHEMICAL SENSOR AND METHOD

TECHNICAL FIELD

The present invention relates to chemical sensors and, more particularly, to optical chemical vapor sensors of the type utilizing an absorber/expander material to influence light propagation in a fiber optic waveguide.

BACKGROUND ART

Many different types of optical chemical sensors utilize an absorber/expander material, such as for example silicone rubber, to detect the presence of a particular chemical analyte, such as a hydrocarbon, in either a liquid, vapor or gas state. Examples of such sensors can be found in the following U.S. Pat. No. 4,596,443 to Diemeer, et al., No. 4,842,783 to Blaylock, and No. 5,015,843 to Seitz et al. My prior U.S. Pat. No. 5,378,889 discusses these patents and provides more detail on the use of red silicone rubber as an absorber/expander material, and is incorporated herein by reference.

As set forth in the above prior art, absorber/expanders, such as red silicone rubber, can be employed to bend or displace optical waveguides, with the resulting change in flux transmission being sensed and/or measured to determine the presence and location of the chemical analyte. Such systems are particularly well suited for applications in which the absorber/expander is immersed in or contacted by a liquid analyte.

Gas-borne or vapor chemical analytes pose additional problems because their concentration levels are lower. Moreover, in some applications it is very important to relatively rapidly sense changes in analyte concentrations, which becomes even more difficult if the chemical analyte is an air or gas-borne vapor. Mechanically coupling an absorber/expander to an optical waveguide, for example as set forth in my U.S. Pat. No. 5,378,889, further slows the sensor response time.

One application for a chemical vapor sensor system which poses particular problems is in the detection of air leakages in a hydrocarbon vapor recovery system. Thus, it is common for fuel pump assemblies to include a vapor recovery system which draws air-borne hydrocarbons back to the original fuel reservoir as the liquid fuel is being pumped into a vehicle's fuel tank. If the recovery system leaks air, for example, when the user fails to hold the nozzle seal squarely against the input conduit to the vehicle fuel tank, hydrocarbon vapor will escape to atmosphere.

Detection of air leaks in such a hydrocarbon vapor recovery system can be used, for example, to alert the user to create a better seal or even to shut the pump down. Such detection must occur rapidly and under rather difficult sensing conditions.

Accordingly, it is an object of the present invention to provide a chemical sensor and method for its use which is adaptable to a wide range of applications, is suitable for sensing gas-borne chemical analytes and is rapid in its response to changes in analyte concentrations.

DISCLOSURE OF INVENTION

Briefly described, the present invention comprises a chemical sensor including a light source operable to generate a light flux along a light path, and an optical detector positioned along the light path for receiving the light flux and operable to sense changes in the intensity of the light flux. The light source and optical detector are preferably mounted in spaced relation to each other in a holder or framework which defines a space positioned between the light source and the optical detector. The light flux has to travel through the space in order to reach the optical detector. An absorber/expander member is carried by the holder and positioned in the space between the light source and detector to act as a shutter for the light flux. Thus, the absorber/expander has an edge, preferably a lower end, that is located adjacent the path of travel of the light flux, and the absorber/expander is supported in a manner permitting freedom of movement of the edge or lower end across the light path. The absorber/expander is made of a material that changes size by either expanding or contracting in the presence of a preselected chemical analyte or component. In use, the light flux passes underneath the lower end of the absorber/expander which preferably obstructs approximately one-half of the light flux when the absorber/expander is in a contracted state, and in its expanded state, the absorber/expander obstructs a greater amount of the light flux, causing changes in intensity of the light flux that reaches the optical detector. In the most preferred form, the absorber/expander is a relatively thin sheet of red silicone rubber which is suspended by an upper end and is gravity biased to hang with its lower end or edge at about the mid-point of the flux being transmitted to the detector.

The optical detector is adapted to provide an output signal when light flux reaching the optical detector decreases or increases. Red silicone rubber is a particularly effective absorber/expander of gas-borne hydrocarbons in that it expands and contracts rapidly in proportion to the concentration of the hydrocarbon vapor.

According to a preferred aspect of the invention, the optical assembly includes a first optical fiber waveguide optically communicating from the light source to the space in which the absorber/expander shutter is mounted and a second optical fiber waveguide optically communicating from the space to the detector. The light flux travels through the optical fiber waveguides before and after traveling past the absorber/expander. The optical fiber waveguides have the effect of better coupling or focusing the light flux across the space in order to increase the rate of flux attenuation per unit movement of the absorber/expander shutter.

According to one embodiment of the absorber/expander, the absorber/expander is provided with a constant cross-section along its length. In another embodiment, the absorber/expander is tapered toward its lower end. In a third embodiment, the absorber/expander includes a smaller thickness region and a larger thickness region. The smaller thickness region extends from the lower end of the absorber/expander. This last embodiment provides the best sensitivity.

In another aspect of the present invention, a method of detecting a chemical analyte is provided which is comprised, briefly, of the steps of transmitting light flux from a light source past a shutter-like absorber/expander member to an optical detector, exposing the absorber/expander to a change in the amount of chemical analyte contacting the absorber/expander to produce movement of an edge of the absorber/expander and thus change the light flux received by the detector, and sensing the change in light flux using the optical detector.

These and other features, objects, and advantages of the present invention will become apparent from the following description of the best mode for carrying out the invention, when read in conjunction with the accompanying drawings, and the claims, which are all incorporated herein as part of the disclosure of the invention.

BRIEF DESCRIPTION OF THE DRAWINGS

Throughout the several views, like reference numerals refer to like parts, wherein:

FIG. 1 is a schematic representation illustrating the basic embodiment of a chemical vapor sensor constructed in accordance with the present invention;

FIG. 2 is a schematic representation illustrating an alternative embodiment of the sensor of FIG. 1;

FIG. 3 is a pictorial view of the absorber/expander member of FIG. 1 and its frame support;

FIG. 4 is a pictorial view of the assembled absorber/expander of FIG. 3 and a holder therefor;

FIG. 5 is an enlarged front elevation view of an alternative embodiment of the absorber/expander member shown with its frame support in section;

FIG. 6 is a side elevation view in cross section of the absorber/expander member of FIG. 5 taken substantially along the plane of line 6—6 in FIG. 5;

FIG. 7 is a front elevation view of the absorber/expander of FIGS. 5 and 6;

FIG. 8 is a side elevation view of the absorber/expander of FIG. 7;

FIG. 9 is a front elevation view of further embodiment of the absorber/expander;

FIG. 10 is a side elevation view of still a further alternative embodiment of the absorber/expander.

BEST MODE OF CARRYING OUT THE INVENTION

Reference will now be made in detail to the preferred embodiments of the invention, examples of which are illustrated in the accompanying drawings. While the invention will be described in conjunction with the preferred embodiments, it will be understood that the described embodiments are not intended to limit the invention specifically to those embodiments. On the contrary, the invention is intended to cover alternatives, modifications and equivalents, which may be included within the spirit and scope of the invention as defined by the appended claims.

Referring to FIG. 1, the present invention comprises a chemical sensor, indicated generally by reference numeral 11, which includes a light source 12, that may for example be an LED, and an optical detector 14, which may for example be a photodiode. Optical source 12 is operable to generate a light flux bundle 16 that is directed along a light path toward optical detector 14. Light source 12 and optical detector 14 are spaced apart to provide for positioning of an absorber/expander sensor element or member 18 therebetween. Absorber/expander sensor element 18 is carried by a frame support or holder 20. When sensor 11 is to be used to sense the presence of hydrocarbons and particularly volatile hydrocarbons, absorber/expander sensor element 18 advantageously may be made from RTV 159 red silicone rubber. This polymer material is discussed in more detail in my prior U.S. Pat. No. 5,378,889, which is incorporated herein by reference. The absorber/expander material must be one which will change its dimensions as a result of absorbing and emitting the chemical analyte to be sensed, and red silicone rubber is particularly well suited for sensing hydrocarbon vapor, such as gasoline vapor in that it changes its dimensions by a substantial amount and the change occurs relatively rapidly in thin cross-sections.

Absorber/expander sensor element 18 is positioned where it will be exposed to contact with the particular chemical component, such as for example hydrocarbon fuel vapors. In the presence of such vapor, sensor element 18 expands in a manner where an edge, in this embodiment lower end 22, of the sensor element moves, in this case downwardly, into the light path of flux bundle 16. In its expanded condition, lower end 22 of sensor element 18 at least partially blocks light flux 16, attenuating light flux 24 transmitted to photodiode detector 14. Optical detector 14 is operable to sense light flux changes, and is responsive to a change in intensity of light flux 24 to generate an output signal 26 for use in indicating the present of the target or analyte vapor.

Alternatively, absorber/expander element 18 can be employed in a manner in which the sensor element is in an expanded condition in the presence of a chemical component, and contracts in the absence of that chemical component or in the presence of an additional chemical component or analyte. The contraction of the sensor element at least partially removes the obstruction of the sensor element, increasing the light intensity transmitted to the photodiode. Most preferably, sensor element 18 obstructs about one-half of light flux 16 before movement induced by the presence or absence of the target analyte. This enhances the sensitivity of sensor assembly 11.

Broadly, therefore, sensor assembly 11 of the present invention employs a shutter-like absorber/expander 18 which at least partially interrupts the light flux transmission to a flux intensity sensor 14. As a target analyte, to which the absorber/expander 18 is sensitive, contacts the absorber/expander, the absorber/expander expands and an edge 22 thereof is substantially unconstrained and is free to move across light path 16 and change the amount or intensity of flux 24 reaching detector 14.

As will be set out in more detail below, chemical sensor apparatus 11 is particularly well suited for vapor sensing. Thus, absorber/expander 18 may advantageously be provided by a thin sheet of material having a relatively large surface area and yet being sufficiently thin that absorption of chemical analyte will produce a relatively rapid expansion and thus movement of lower edge 22 of the shutter. It would be possible, however, to employ the shutter-based system of the present invention to sense the presence of a liquid chemical analyte.

When using an absorber/expander as a shutter across the light path, it is not necessary that absorber/expander 18 be opaque. Red silicone rubber in thin sections (for example, 0.5 millimeters) is translucent rather than opaque, but the light flux transmitted through member or element 18 is significantly less than when light flux 16 is unobstructed. Thus, as edge 22 moves, optical detector 14 can readily detect flux density changes.

FIG. 2 illustrates optical circuit 28 of sensor 11 of the present invention. LED 12 and photodiode 14 each have associated with it an optical fiber waveguide 30, 32, respectively. Preferably, each optical fiber waveguide is 1 mm PMMA fiber. Optical fiber waveguide 30 couples the light flux from LED 12 into a tighter bundle, focusing the light flux transmitted past an upper edge of sensor element 18', and optical fiber 32 couples the transmitted light flux received by photodiode 14 into a tighter acceptance cone. Coupling of the light flux using fiber waveguides has the effect of increasing the rate of flux attenuation per unit movement of the upper end 22 of absorber/expander member 18'.

FIG. 2 shows the flux path 36 of the transmitted light flux. Flux path 36 is also referred to as the light path of the light flux. It is preferable to couple or focus the light transmitted along flux path 36 as tightly as possible in order to decrease the extent to which the lower end of the absorber/expander element has to expand or contract in order to effect a change in light flux intensity which can be sensed. Even with optical fiber waveguides 30, 32, the shape of the transmitted light flux will be dispersed somewhat, allowing for partial obstruction of the light flux by the absorber/expander element.

As will be seen, absorber/expander 18 is mounted in an orientation in which an upper edge 22 moves to act as a shutter across flux path or light path 36. In most applications, it is highly desirable to provide an absorber/expander which is very thin and has an edge 22 which is free to move upon absorption or emission of the target analyte. Thin sections provide faster response time, but they also make it more difficult for the absorber/expander to be oriented for an upper edge 22 to act as a shutter. Nevertheless, a triangular cross-section can be used, and it is contemplated that the shutter edge which interrupts the light path may be an upper, lower or side edge of an absorber/expander member.

It is generally easier, however, to support or suspend elongated, thin sheets of absorber/expander material from proximate an upper end thereof and allow them to be gravity biased in a near vertical orientation down across the flux path. Thus, as shown in FIGS. 3 and 4, a thin sheet 18 of red silicone rubber (RSR) is supported by a rod 48 which extends transversely through and is adhesively secured to sheet absorber/expander 18. Frame support 20 for the absorber/expander may have an inverted U-shape which includes a pair of legs 42 joined by an upper bridge section 44. A groove 46 is formed on one side of each leg 42 for receiving cylindrical rod support 48. Rod support 48 is longer than sensor element 18 is wide and is approximately as wide as frame support 20. Sensor element 18 is centered on and adhesively secured to rod support 48, which in turn is adhesively secured within grooves 46. Rod support preferably is made of glass since it can be easily adhesively bonded to RTV red silicon rubber (both materials being silicone-based).

As shown in FIG. 4, frame support 20 and absorber/expander sensor element 18, as a unit, are positioned within a vertically extending slot 40 in a body or housing 38 of chemical sensor assembly 11 and secured in place by a set screw 49. Body 38 includes a pair of aligned openings 50 (only one shown) extending through to slot 40, one for receiving LED 12 and its associated optical fiber waveguide 30 and one for receiving photodiode 14 and its associated optical fiber waveguide 32. Openings 50 preferably position waveguides 30 and 32 so that shutter edge 22 is at about the mid-height of the light path between the waveguides for the steady state, normal or target operating conditions of the absorber/expander. Thus, for applications in which no analyte is present, the absorber/expander is fully contracted at about the mid-height of the flux path. In an application in which vapor is present, absorber/expander 18 will be fully expanded and at mid-height of the flux path.

FIGS. 5 and 6 illustrate the tapered design for sensor element 18 shown in FIG. 2, but with the sensor element again supported from above by rod 48. The wide end 54 of sensor element 18' is adhesively secured to glass rod support 48 and the tapered end 56 terminates at an edge, which forms the lower end 22 of the element. Preferably, frame support 20 is made of a structural plastic, such as polyvinyl chloride (PVC) or polyoxy methylene acetal resin (DELRIN). For a hydrocarbon fuel vapor detecting application, frame support 20 may, for example, have dimensions of 8 mm width, 16 mm height, and 2 mm depth.

FIGS. 7 and 8 provide a corresponding example for the dimensions of sensor element 18'. The sensor element may be approximately 5 mm in width, 10 mm in height and 2 mm in depth at wide end 54. The approximate diameter of rod support 48 is 5 mils.

FIG. 9 illustrates an alternative embodiment for the sensor element. In FIG. 9, an absorber/expander sensor element 18" includes cut-out sections 58, 60, which are defined by mounting extensions 64, 66, 68. Rod support 48 is adhesively secured within a transverse bore in mounting extensions 64, 66, 68. With this version of the sensor is element, lateral expansion of the sensor element is reduced.

FIG. 10 illustrates a further alternative embodiment for the sensor element 18'''. In FIG. 10, a sensor element 18''' is not tapered, but has a width reduced to approximately 0.5 mm. An enlarged mounting block 72 is provided for securing sensor element 18''' to rod support 48. It has been found that the design of sensor element 18''' provides improved sensitivity as compared to the sensor element of FIG. 4. In other words, it has a higher coefficient of expansion for a given concentration of the targeted chemical component.

In order to better support the thin sheets which are advantageously used as absorber/expander members in the present apparatus, it is advantageous to provide hinge supports 52 (FIG. 4), preferably two on each side of sensor element 18. Each hinge support 52 is secured at its outer end to a leg 42 of frame support 20 and at its inner end directly to the sensor element. Hinge supports 52 allow the sensor element to expand downwardly or contract upwardly, while minimizing sagging and lateral sway of the thin sheets sensor element. Hinges 52 can be provided by flexible RTV red silicon rubber rods which are adhesively secured at their ends to the frame and sensor member.

Various other materials and forms of red silicone rubber can be utilized with the present invention. The material selected for the sensor element should exhibit a unique coefficient of expansion for a particular vapor. Also, the fact that different vapors exhibit unique coefficients of expansion to various forms of red silicone rubber provides the ability to identify a particular vapor specie. This can be accomplished by monitoring a multiplicity of different absorber/expander materials. The different output signals from the various absorber/expander materials are used to form a vector input to a neural network, the details of which are not part of the present invention and, being well understood in the art, are not discussed herein. One type of vector provides a value indicative of the light flux intensity and another type of vector provides a value for the rate of change in the light flux signal at any moment. These two vector types are used to determine or identify the particular vapor present at a sensor element. It should also be noted that a single sensor element material can be used to detect the presence of a broad range of vapors.

An exemplary application for the foregoing sensor elements is for use in detecting the presence of air in vapor recovery systems. In such a system, a particular vapor, such as for example a hydrocarbon fuel vapor, is extracted from a fuel reservoir and pumped into a vehicle tank. Should air be pulled into the system during the vapor extraction process, the sensor element reacts to the presence of air by contracting. This has the affect of partially unobstructing the light flux, thus increasing the light flux transmitted to the photodiode. The increased light flux is utilized to generate a corresponding output signal to signal the presence of air in the system.

The present invention also includes a method of detecting changes in the amount of chemical analyte present at a chemical sensor. The method includes the steps of transmitting light flux 16 from a light source 12 to an optical detector 14 along a light or flux path 36 which is at least partially interrupted by a shutter-like absorber/expander member 18. The absorber/expander 18 has a movable edge 22 and for hydrocarbon vapor sensors is most preferably provided by a relatively thin sheet of red silicone rubber. The next step in the process is exposing the absorber/expander member to a change in the amount of chemical analyte, most preferably a hydrocarbon vapor, contacting the absorber/expander, which produces one of expansion and contraction of absorber/expander 18 to move the position of edge 22 of the shutter (the absorber/expander) relative to light path 16. Finally, the present method includes the step of sensing changes in the intensity of light flux 24 reaching optical detector 14 as a result of movement of edge 22 of the absorber/expander.

In order to enhance sensitivity, the transmitting step is most preferably accomplished by transmitting light flux through optical fiber waveguides on each side of the absorber/expander.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto when read and interpreted according to accepted legal principles such as the doctrine of equivalents and reversal of parts.

What is claimed is:

1. A chemical sensor comprising:
   a light source operable to generate a light flux along a light path;
   an optical detector positioned along the light path in spaced relation to the light source to receive the light flux, the detector being operable to sense changes in the intensity of the light flux;
   an absorber/expander positioned between the light source and the optical detector and having an edge thereof supported for movement across at least a portion of said light path to change the intensity of the light flux sensed by the optical detector, the absorber/expander being made of a material that expands in the presence of a preselected chemical analyte and contracts in the absence of the chemical analyte to produce movement of the edge and changes in the intensity of the light flux sensed by the optical detector by an amount proportional to the amount of chemical analyte present at the absorber/expander.

2. The chemical sensor as defined in claim 1 wherein, the absorber/expander is made from a red silicone rubber.

3. The chemical sensor as defined in claim 1, and
   a holder,
   the absorber/expander being mounted in the holder with the edge substantially constrained for movement across the light path.

4. The chemical sensor as defined in claim 3 wherein, the holder mounts the absorber/expander for absorption of an air-borne chemical analyte.

5. The chemical sensor as defined in claim 1 wherein, the absorber/expander has a substantial length dimension perpendicular to the edge relative to the width of the absorber/expander.

6. The chemical sensor as defined in claim 1 wherein, the absorber/expander has a small thickness dimension relative to the length dimension perpendicular to the edge.

7. The chemical sensor as defined in claim 6 wherein, the absorber/expander is made from a red silicone rubber and has a length dimension perpendicular to the edge substantially greater than the width dimension of the edge.

8. The chemical sensor as defined in claim 1, and
   a sensor holder, and
   the absorber/expander being elongated and mounted to the holder and depending downwardly therefrom so that the edge is a lower end of the absorber/expander.

9. The chemical sensor as defined in claim 8 wherein, the absorber/expander is mounted for articulation to the holder and is gravity biased to a near vertical position with the lower end intersecting about one-half of the light path when the chemical analyte to be sensed is present at the absorber/expander in about a target amount.

10. The chemical sensor as defined in claim 9 wherein, the absorber/expander is a sheet of RTV red silicon rubber having a length dimension about twice a width dimension and a thickness dimension not greater than about one-tenth the length dimension.

11. A chemical sensor for sensing the presence of a gas-borne chemical analyte, comprising:
    a holder;
    an optical circuit carried by the holder, the optical circuit including a light source operable to generate a light flux along a light path, and an optical detector mounted to the holder in spaced relation to the light source in a position along the light path to receive the light flux, the optical detector being operable to sense changes in the intensity of the light flux received; and
    an absorber/expander carried by the holder in a position along the light path and between the light source and the optical detector, the absorber/expander being further carried by the holder in a position exposing the absorber/expander to the gas carrying the chemical analyte, the absorber/expander being made of a material that expands and contracts in the presence and absence of the chemical analyte, the absorber/expander having an edge that is located adjacent the light path, and the absorber/expander being held by the holder in a manner permitting freedom of movement of the edge of the absorber/expander, wherein the light flux passes beyond the edge of the absorber/expander when the absorber/expander is in a contracted state, and in an expanded state, the absorber/expander obstructs the light flux, causing a change in intensity of the light flux that reaches the optical detector.

12. The sensor as defined in claim 11 wherein, the light flux generated by the light source has a width sufficient to allow the absorber/expander to move partially into the light path, and the optical detector is adapted to provide an output signal when light flux reaching the optical detector decreases or increases to a predetermined intensity.

13. The sensor as defined in claim 12 wherein, the absorber/expander is made of a material that expands or contracts in proportion to the intensity of the chemical analyte present in the gas contacting the absorber/expander.

14. The sensor as defined in claim 11 wherein, the light source includes a first optical fiber waveguide optically communicating with a space in which the absorber/expander is mounted, defined by the holder, and the optical detector includes a second optical fiber waveguide optically communicating with the space in which the absorber/expander is mounted, so that the light flux travels through the optical fiber waveguides before and after traveling beyond the absorber/expander.

15. The sensor as defined in claim 11 wherein, the absorber/expander is held by an optical fiber support.

16. The sensor as defined in claim 11, and further comprising:

hinge supports for supporting lower regions of the absorber/expander, the hinge supports permitting expansion and contraction of the absorber/expander.

17. The sensor as defined in claim 11 wherein, the absorber/expander has a constant cross-section along its length.

18. The sensor as defined in claim 11 wherein, the absorber/expander is tapered toward the edge.

19. The sensor as defined in claim 11 wherein, the edge is a lower end of the absorber/expander and the absorber/expander includes a smaller thickness region and a larger thickness region, the smaller thickness region extending from the lower end of the absorber/expander.

20. The sensor as defined in claim 11 wherein, the absorber/expander includes cut-out regions adjacent the holder.

21. The sensor as defined in claim 11 wherein, the absorber/expander is red silicone rubber.

22. The method detecting changes in the amount of a chemical analyte present at a chemical sensor comprising the steps of:

transmitting light flux from a light source to an optical detector of a chemical sensor along a light path at least partially interrupted by an absorber/expander member having a movable edge extending across the light path;

exposing the absorber/expander member to a change in the amount of chemical analyte in contact with the absorber/expander member to produce one of expansion and contraction of the absorber/expander member and movement of the position of the edge relative to the light path; and sensing with the optical detector the change in intensity of the light flux reaching the optical detector resulting from movement of the edge of the absorber/expander member during expansion and contraction of the absorber/expander member.

23. The method as defined in claim 22 wherein, the transmitting step is accomplished by transmitting light flux along a light path interrupted by the edge of a red silicone rubber absorber/expander member.

24. The method as defined in claim 23 wherein, the transmitting step is accomplished by transmitting light flux under a lower edge of a sheet of red silicone rubber suspended proximate an upper edge and gravity biased to a near vertical orientation extending at least partially across the light path.

25. The method as defined in claim 24 wherein, the exposing step is accomplished by exposing the sheet of red silicone rubber to a gas-borne hydrocarbon analyte.

26. The method as defined in claim 22 wherein, the transmitting step is accomplished by transmitting the light flux up to the absorber/expander member through an optical fiber waveguide and transmitting the light flux from the absorber/expander to the optical detector through an optical fiber waveguide.

* * * * *

UNITED STATES PATENT AND TRADEMARK OFFICE
CERTIFICATE OF CORRECTION

PATENT NO. : 5,796,097

DATED : August 18, 1998

INVENTOR(S) : William R. Lawrence

It is certified that error appears in the above-identified patent and that said Letters Patent is hereby corrected as shown below:

On the cover sheet, Section [56] delete "5,379,889" and insert therefor --5,378,889--.

Signed and Sealed this

Twenty-fourth Day of November,1998

Attest:

BRUCE LEHMAN

Attesting Officer     Commissioner of Patents and Trademarks